United States Patent
St. Cyr

[11] Patent Number: 5,250,052
[45] Date of Patent: Oct. 5, 1993

[54] SUTURE REMOVAL TOOL

[76] Inventor: John A. St. Cyr, 10405 45 Ave. N. Apt 216, Plymouth, Minn. 55442

[21] Appl. No.: 973,649

[22] Filed: Nov. 9, 1992

[51] Int. Cl.$^5$ ............................................. A61B 17/00
[52] U.S. Cl. ................................... 606/138; 112/169; 30/123.3
[58] Field of Search ...................... 606/138, 167, 190; 112/169; 30/123.3, 314, DIG. 3

[56] References Cited

U.S. PATENT DOCUMENTS

| | | | |
|---|---|---|---|
| 3,879,846 | 4/1975 | Allen, Jr. | 606/138 |
| 3,961,419 | 6/1976 | Schwartz | 606/138 |
| 4,053,979 | 10/1977 | Tuthill et al. | 606/138 |
| 4,802,478 | 2/1989 | Powell | 606/138 |
| 5,047,037 | 9/1991 | Brandfield | 606/138 |

Primary Examiner—Stephen C. Pellegrino
Assistant Examiner—Tamara L. Graysay
Attorney, Agent, or Firm—Leon Gilden

[57] ABSTRACT

A tool structure employs a rectilinear body having a front wall, the front wall including a lowermost end orthogonally oriented relative to the front wall and extending beyond a bottom wall in an orthogonal relationship, wherein the lowermost end of the front wall includes a plurality of rods arranged in a parallel relationship relative to one another, and the first rod having a first hook, the second rod of the plurality of rods having a cutting edge therewithin, whereupon the hook permits lifting and the cutting edge effects severing of sutures.

5 Claims, 4 Drawing Sheets

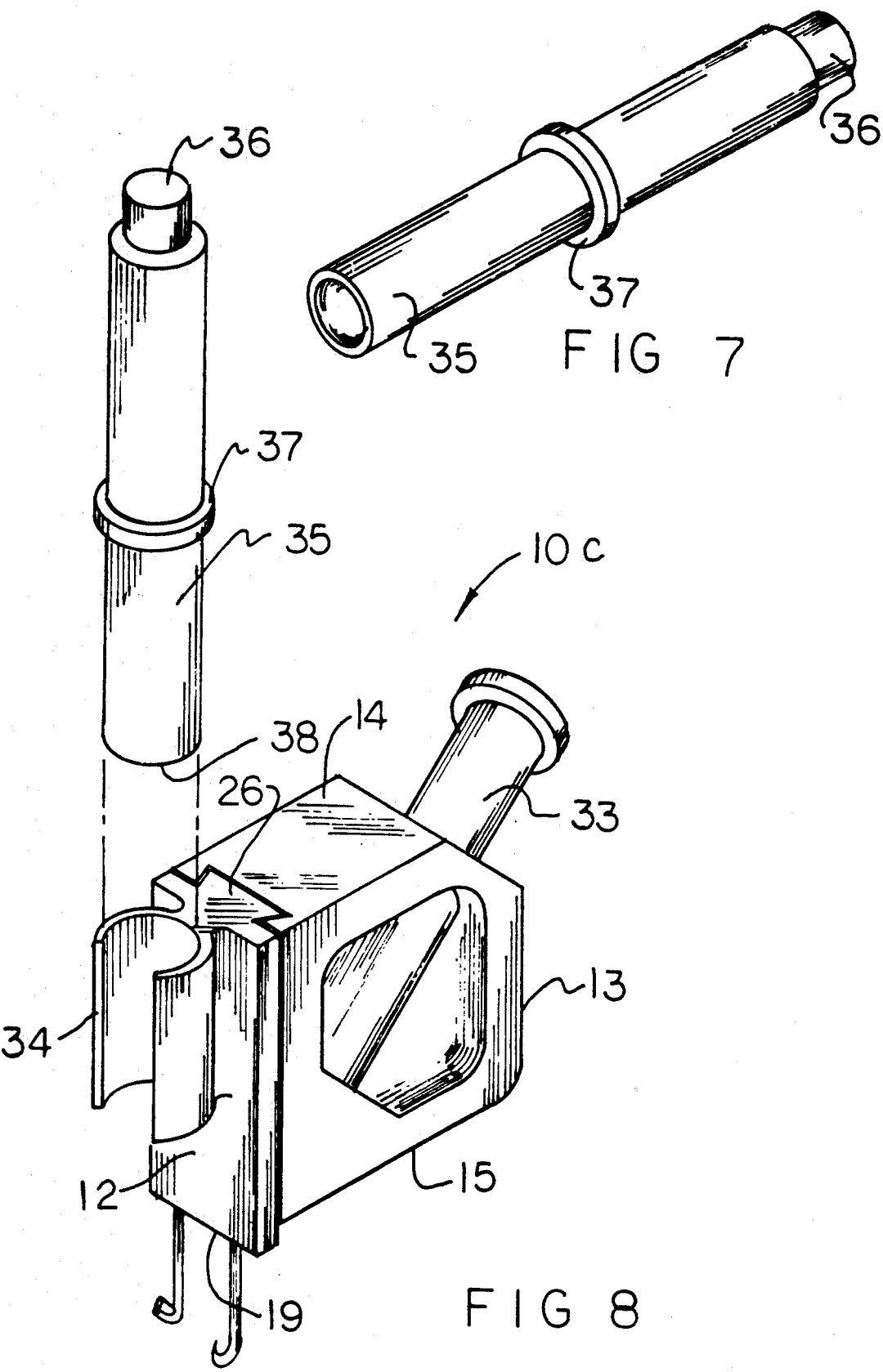

SUTURE REMOVAL TOOL

BACKGROUND OF THE INVENTION

1. Field of the Invention

The field of invention relates to suture tool structure, and more particularly pertains to a new and improved suture removal tool effecting the removal of sutures relative to an individual.

2. Description of the Prior Art

Suture tools of various types have been utilized throughout the prior art and removal tool structure is indicated in the U.S. Pat. Nos. 5,047,037; 4,802,478; 3,879,846; and 4,053,979.

The prior art has heretofore failed to provide for an organization as indicated in the instant invention addressing the simultaneous lifting and severing of a suture organization and in this respect, the present invention substantially fulfills this need.

SUMMARY OF THE INVENTION

In view of the foregoing disadvantages inherent in the known types of suture tool structure now present in the prior art, the present invention provides a suture removal tool wherein the same employs a lift and cutter structure relative to the organization for the severing and removal of sutures relative to an individual. As such, the general purpose of the present invention, which will be described subsequently in greater detail, is to provide a new and improved suture removal tool which has all the advantages of the prior art suture tool structure and none of the disadvantages.

To attain this, the present invention provides a tool structure employing a rectilinear body having a front wall, the front wall including a lowermost end orthogonally oriented relative to the front wall and extending beyond a bottom wall in an orthogonal relationship, wherein the lowermost end of the front wall includes a plurality of rods arranged in a parallel relationship relative to one another, and the first rod having a first hook, the second rod of the plurality of rods having a cutting edge therewithin, whereupon the hook permits lifting and the cutting edge effects severing of sutures.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregiong abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved suture removal tool which has all the advantages of the prior art suture tool structure and none of the disadvantages.

It is another object of the present invention to provide a new and improved suture removal tool which may be easily and efficiently manufactured and marketed.

It is a further object of the present invention to provide a new and improved suture removal tool which is of a durable and reliable construction.

An even further object of the present invention is to provide a new and improved suture removal tool which is susceptible of a low cost of manufacture with regard to both materials and labor, and which accordingly is then susceptible of low prices of sale of the consuming public, thereby making such suture removal tools economically available to the buying public.

Still yet another object of the present invention is to provide a new and improved suture removal tool which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is an isometric illustration of a flashlight member utilized by the invention, as indicated in FIG. 8.

FIG. 8 is an isometric illustration of a yet further modified aspect of the invention employing the flashlight structure as set forth in FIG. 7.

DESCRIPTION OF THE PREFERRED EMBODIMENT

Figure 1:
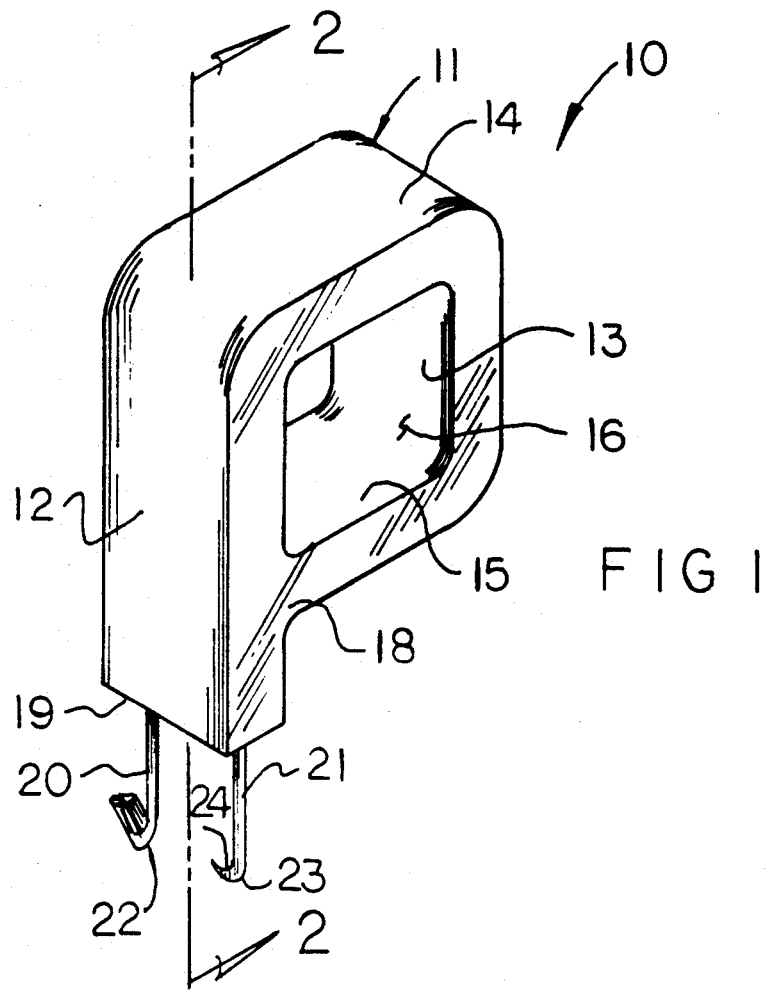
FIG. 1 is an isometric illustration of the instant invention.
Figure 2:
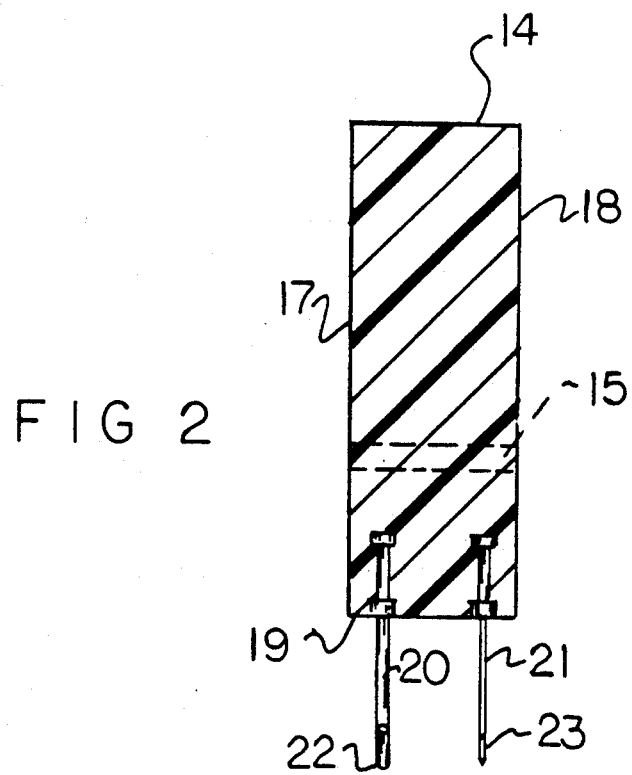
FIG. 2 is an orthographic view, taken along the lines 2—2 of FIG. 1 in the direction indicated by the arrows.

With reference now to the drawings, and in particular to FIGS. 1 to 8 thereof, a new and improved suture removal tool embodying the principles and concepts of the present invention and generally designated by the reference numerals 10, 10a, 10b, and 10c will be described.

More specifically, the suture removal tool 10 of the instant invention, as indicated in FIG. 1, includes a support housing 11 having a front wall 12 spaced from and parallel a rear wall 13, with a top wall 14 spaced from and parallel a bottom wall 15. The front wall 12 extends orthogonally and beyond the bottom wall 15 terminating in a front wall end wall 19. A handle opening 16 is directed medially and through-extending the support housing 11 as indicated, with the support housing 11 terminating in parallel first and second side walls 17 and 18 respectively. Fixedly and orthogonally mounted to the front wall end wall 19 are respective first and second rods 20 and 21 positioned parallel to and adjacent the respective first and second side walls 17 and 18. The first and second rods 20 and 21 are parallel relative to one another and are each of a predetermined length, with the first rod 20 terminating in a first rod hook 22 for lifting and securing a suture member (see FIG. 4) within the restricted first rod hook 22. The second rod 21 includes a second rod hook 23 having a cutter blade 24 therewithin to provide for simultaneous severing of the suture.

Figure 3:
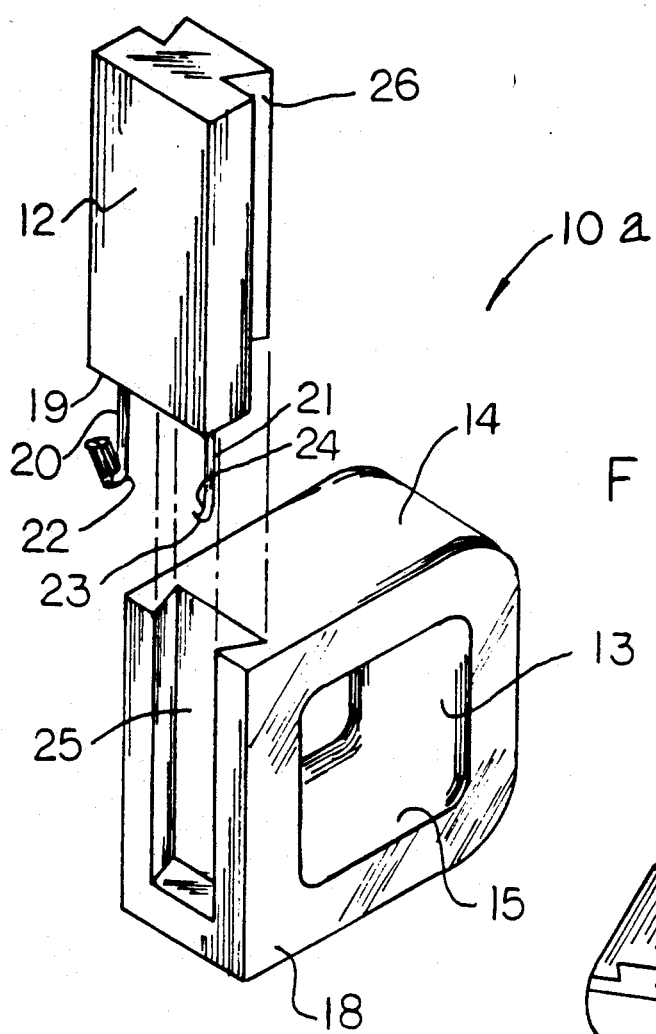
FIG. 3 is an isometric illustration of a modified aspect of the invention.

The FIG. 3 indicates the tool structure 10a, wherein the front wall 12 includes a dove tail projection 26 having a projection length received within a dove tail groove 25, having a groove length substantially equal to the projection length. The dove tail projection is received within a dove tail groove to orient the front wall end wall 19 below the bottom wall 15. In this manner, replacement first and second rod structure 20 and 21 may be provided due to inadvertent breakage and the like of the structure permitting ease of maintenance of the organization.

Figure 4:
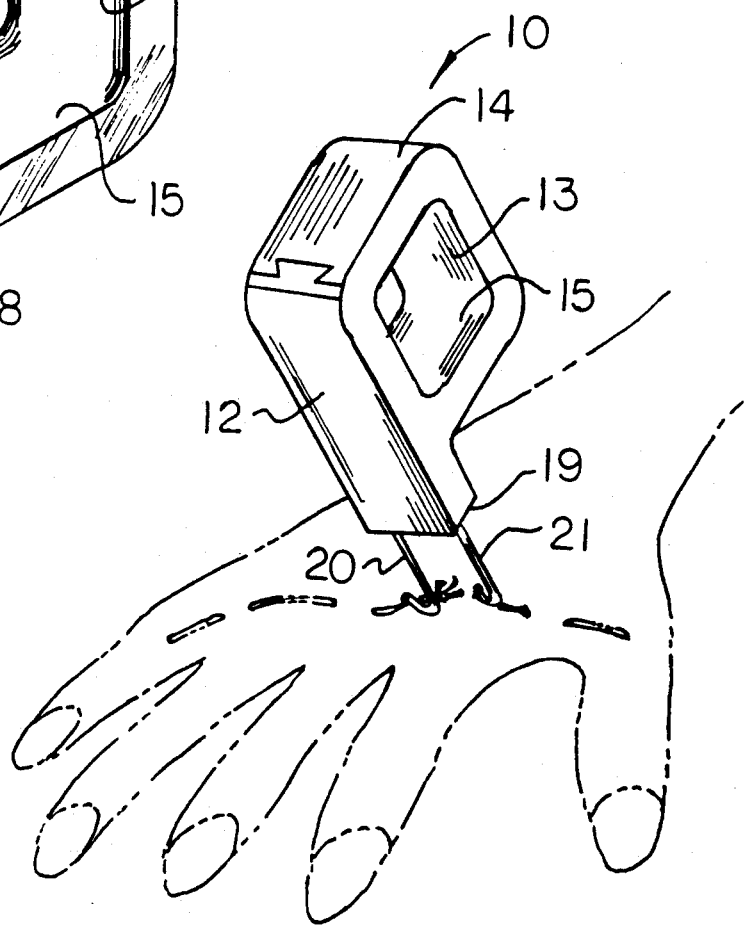
FIG. 4 is an isometric illustration of the invention in use.
Figure 5:
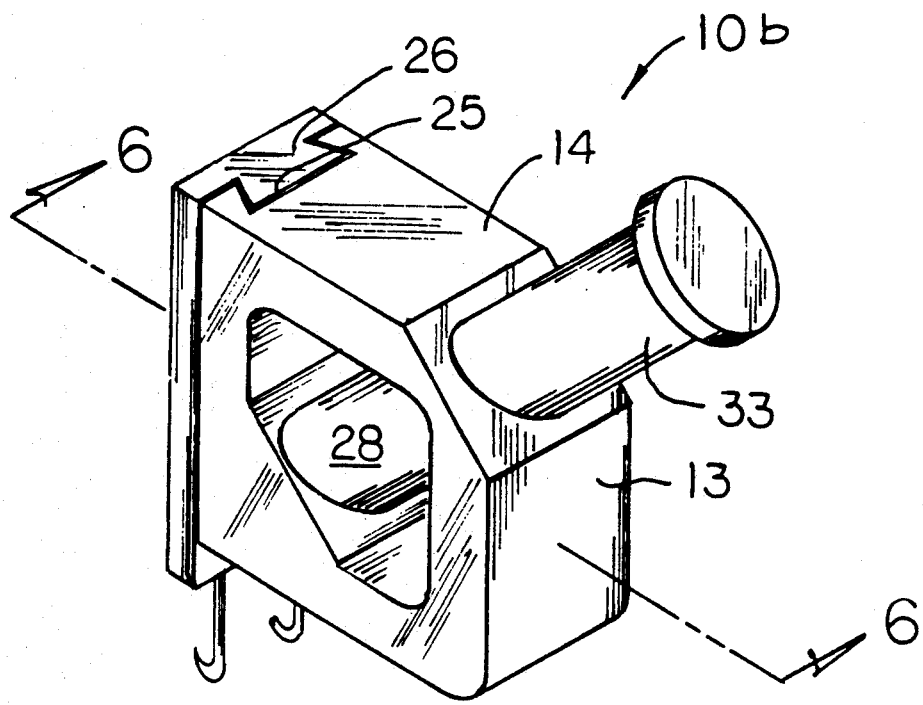
FIG. 5 is an isometric illustration of a further modified aspect of the invention.
Figure 6:
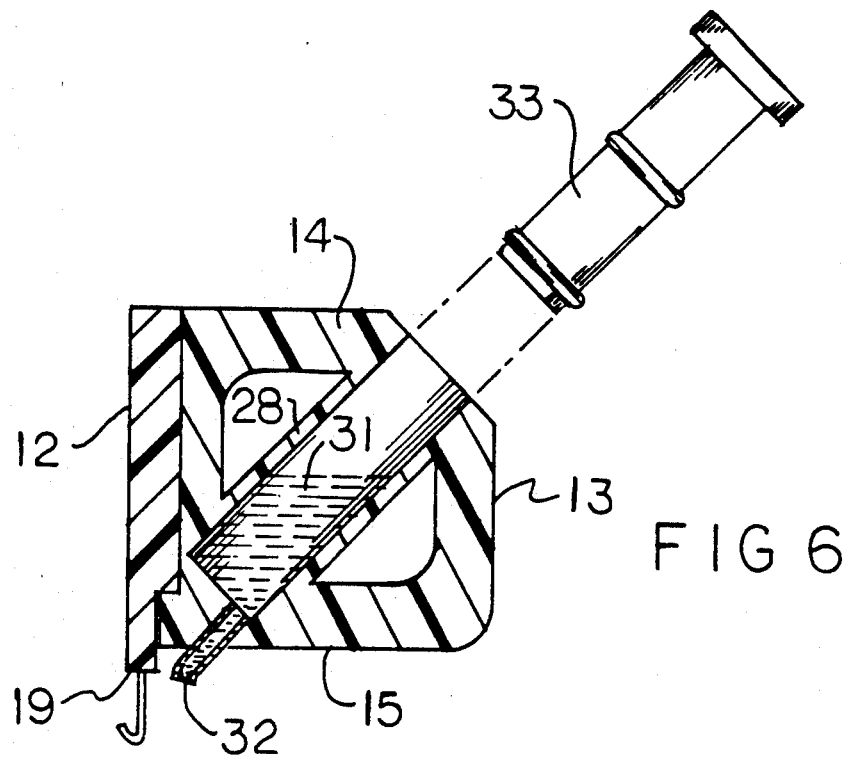
FIG. 6 is an orthographic view, taken along the lines 6—6 of FIG. 5 in the direction indicated by the arrows.

The FIG. 5 indicates the tool structure 10b further employing a tubular fluid reservoir 28 directed through an intersection of the top wall and rear wall 14 and 13 respectively. The tubular fluid reservoir 28 extends through the handle opening 16 and is oriented at substantially an acute angle relative to the bottom wall 15, with an outlet port 32 in fluid communication with a bactericide 31 contained within the fluid reservoir, with the outlet port projecting through the bottom wall in adjacency to the front wall end wall 19. A plunger 33 received within the fluid reservoir 28 permits projection of the bactericide 31 onto the wound about the suture member, as indicated in FIG. 4, to minimize infection upon removal of the suture structure.

The organization 10c, as indicated in FIG. 8, further includes a semi-cylindrical spring ring 34 fixedly mounted to the front wall 12 for reception of a flashlight cylinder 35. The flashlight cylinder includes an on/off plunger 36 at a second end of the flashlight cylinder, with a first end of the flashlight cylinder 38 spaced from an abutment ring 37 positioned fixedly about the flashlight cylinder and spaced therefrom a further predetermined length that is substantially equal to the further predetermined length as measured from the front wall end wall 19 to the top wall 14 to orient the flashlight structure in adjacency to the front wall end wall for ease of viewing and enhanced illumination of the wound area to be treated.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A suture removal tool, comprising,
   a support housing, the support housing including a front wall spaced from a rear wall, a top wall and a bottom wall, and a first side wall spaced from and parallel a second side wall, and
   a handle opening directed through the support housing, and with the handle opening directed orthogonally to the first side wall and the second side wall through-extending the support housing, with the support housing arranged in surrounding relationship relative to the handle opening, and
   the front wall including a front wall end wall spaced below and parallel the bottom wall, and
   the front wall end wall having a first rod and a second rod fixedly and orthogonally mounted to the front wall end wall, with the first rod arranged parallel relative to the first side wall, the second rod oriented parallel to the second side wall, the first rod having a first hook, the second rod having a second hook.

2. A tool as set forth in claim 1 wherein the second hook includes a cutter blade positioned within the second rod hook for severing of a suture positioned within the second rod hook, and the first rod hook is arranged for receiving and securing a suture therewithin.

3. A tool as set forth in claim 2 including the front wall having a dove tail projection, and the support housing having a dove tail groove, the dove tail projection having a projection length, the dove tail groove having a groove length, wherein the projection length is equal to the groove length, and the dove tail projection is arranged for reception within the groove.

4. A tool as set forth in claim 3 including a tubular fluid reservoir directed through the support housing at an intersection of the top wall and the rear wall, and the fluid reservoir having an outlet port, the outlet port directed through the bottom wall positioned in adjacency to the front wall end wall, and a plunger received within the fluid reservoir, and the fluid reservoir arranged for receiving a bactericide therewithin.

5. A tool as set forth in claim 4 including a semicylindrical spring ring mounted to the front wall and a flashlight cylinder, the flashlight cylinder having a first end and a second end, and an abutment ring positioned fixedly about the flashlight cylinder, and the first end spaced from the abutment ring a predetermined length, and the top wall spaced from the front wall end wall said predetermined length.

* * * * *